United States Patent
Raggers et al.

(10) Patent No.: US 7,214,386 B2
(45) Date of Patent: May 8, 2007

(54) METHOD FOR THE TREATMENT AND PREVENTION OF OVERWEIGHT IN MAMMALS

(75) Inventors: Rene John Raggers, Amsterdam (NL); George Verlaan, Wageningen (NL)

(73) Assignee: N.V. Nutricia, MA Zoetermeer (NL)

( * ) Notice: Subject to any disclaimer, the term of this patent is extended or adjusted under 35 U.S.C. 154(b) by 279 days.

(21) Appl. No.: 10/384,750

(22) Filed: Mar. 11, 2003

(65) Prior Publication Data

US 2003/0175368 A1    Sep. 18, 2003

(30) Foreign Application Priority Data

Mar. 11, 2002 (NL) .................... PCT/NL02/00160

(51) Int. Cl.
*A61K 9/20* (2006.01)
(52) U.S. Cl. .................................... 424/464
(58) Field of Classification Search ............... 424/464
See application file for complete search history.

(56) References Cited

U.S. PATENT DOCUMENTS

| | | | |
|---|---|---|---|
| 5,607,715 A * | 3/1997 | Beharry et al. | 426/604 |
| 5,747,053 A * | 5/1998 | Nashimoto et al. | 424/405 |
| 5,798,101 A * | 8/1998 | Haveson | 424/730 |
| 6,280,751 B1 * | 8/2001 | Fletcher et al. | 424/401 |
| 6,299,867 B1 | 10/2001 | Aoyagi et al. | |
| 2002/0176924 A1 * | 11/2002 | Moca et al. | 426/613 |
| 2003/0198659 A1 * | 10/2003 | Hoffman et al. | 424/411 |

FOREIGN PATENT DOCUMENTS

| | | | |
|---|---|---|---|
| EP | 0 914 862 | | 5/1999 |
| EP | 914 862 | * | 5/1999 |
| FR | 2 793 657 | | 11/2000 |

OTHER PUBLICATIONS

GNC Pro Performance Thermo Burst, Tablets, Press release date May 4, 2001.*

* cited by examiner

*Primary Examiner*—Alton Pryor
(74) *Attorney, Agent, or Firm*—Young & Thompson

(57) ABSTRACT

The present invention relates to a method for the prevention and/or treatment of overweight in mammals. More particularly the invention is concerned with such a method comprising the enteral administration to a mammal of a preparation comprising an effective amount of a combination of dill or an isolate thereof and one or more components capable of stimulating in vivo lipolysis. Suitable examples of components capable of stimulating in vivo lipolysis include methylxanthines, adrenergic amines, *Paullinia cupana* or an isolate thereof, *Zingziber officinale* or an isolate thereof, *Camellia sinensis* or an isolate thereof, *Ilex paraguayiensis* or an isolate thereof.

Figure 1:
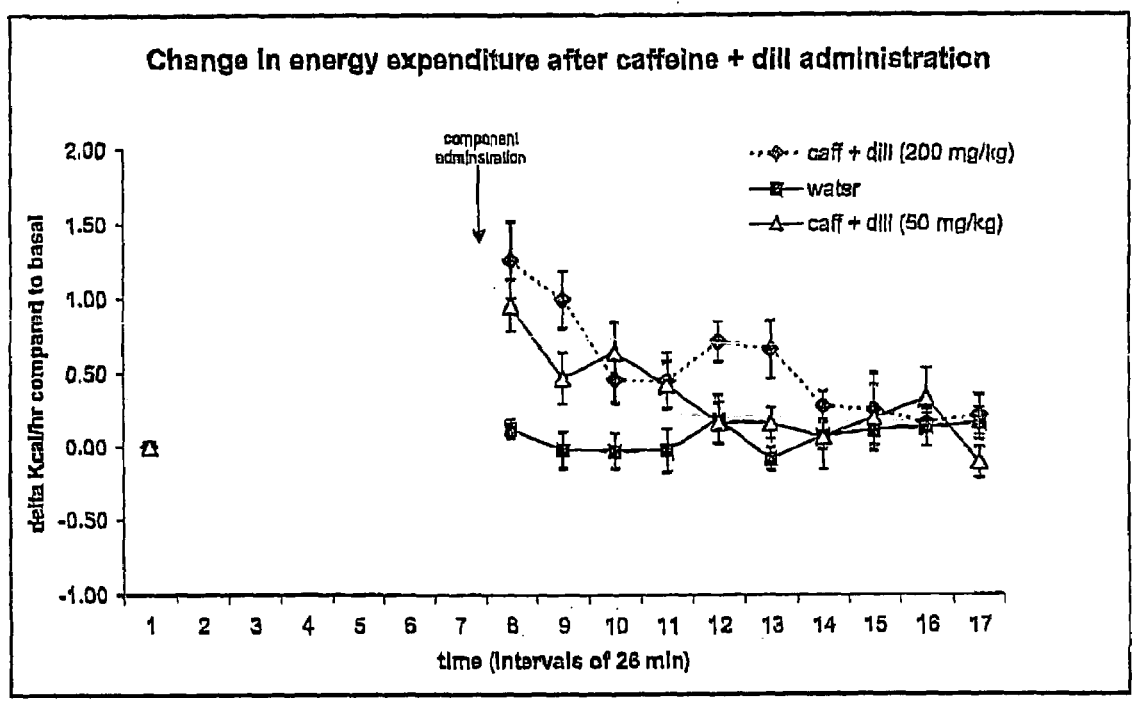

Another aspect of the invention relates to a solid or semi-solid unit dosage, preferably selected from the group consisting of tablets, pills, microparticles, microspheres, suppositories, capsules, caplets and the like, that is suitable for enteral unitary administration to human subjects and other mammals comprising:

a. dill or an isolate thereof in an amount equivalent to between 5 mg and 20 g dill and
   b. a component capable of stimulating in vivo lipolysis.

6 Claims, 3 Drawing Sheets

METHOD FOR THE TREATMENT AND PREVENTION OF OVERWEIGHT IN MAMMALS

FIELD OF THE INVENTION

The present invention relates to a method for the prevention and/or treatment of overweight comprising the enteral administration of a component capable of stimulating in vivo lipolysis. Additionally the present invention provides unit dosages, which can suitably be used for the prophylactic and curative treatment of overweight.

BACKGROUND OF THE INVENTION

Obesity is very common in nowadays society. Approximately 25% to 35% of the population of the Western world is overweight. Overweight is associated with considerable morbidity and mortality. Obesity is the second preventable death cause in de US and a major risk factor for coronary heart disease, hypertension and diabetes mellitus type II. A reduction of body weight with 10% has shown to decrease the risk for coronary heart disease with 20%. Besides this, overweight and/or excess body fat is generally considered a problem, influencing social satisfaction and perception of health.

Attempts to combat overweight are often focussed on alteration of the diet or manipulation of the appetite in order to reduce caloric intake. However, there is accumulating evidence that low energy output predisposes individuals to weight gain and obesity, whether the low energy output is caused by low metabolic rate, physical inactivity or both. Increased energy metabolism therefore is an attractive target for treating overweight. Additionally, it allows people to maintain food intake at socially acceptable levels.

A main function of an adipocyte is the storage of triglycerides for later use as an energy source. The triglycerides can be synthesized from glucose and fatty acids present in the diet. Stimulation of the process in which triglycerides in adipose tissue are hydrolyzed into fatty acids (FA) and glycerol (lipolysis), which are subsequently released in the blood stream and oxidized by tissues in the body to yield energy, results in an increased energy metabolism. Such stimulation of lipolysis in order to mobilize excess stored energy in the form of fat is therefore an attractive mechanism to treat obesity and reduce body fat.

In a natural situation the rate of lipolysis is tightly regulated in the mammalian body, to ensure an adequate supply of energy to tissues at all times, e.g. at times of limited as well as of high demand. Enzymes involved in lipolysis are activated and inactivated by phosphorylation. The changes in phosphorylation state are the result of reversible cAMP-dependent protein phosphorylation reactions that occur at a single serine residue. A further factor contributing to lipolysis of triglycerides in adipose tissue is the translocation of the hormone sensitive lipase (HSL) from the cytosol to the fat droplets. HSL is translocated to the surfaces of the fat droplets as a direct consequence of activation of HSL by phosphorylation. HSL phosphorylation occurs in response to binding of a hormone to a receptor and subsequent activation of cAMP-dependent protein kinase A cascades.

The main endogenous lipolytic agents are the catecholamines, which bind to the adrenergic receptors of adipocytes, thereby initiating the cAMP-dependent cascades in the cell causing increased lipolysis.

Pharmacological interventions with lipolysis stimulating agents (e.g. ephedrine) have been shown to induce body-weight reduction. Ephedrine is both an indirect sympathomimetic causing release of catecholamines (norepinephrine) from sympathetic nerve endings and a direct agonist of beta-adrenergic receptors [Astrup, 1992]. As a consequence, lipolysis is stimulated.

Furthermore, the ingestion of alpha2-adrenoreceptor antagonists, like yohimbine, have been shown to induce lipolytic activity [Galitzki, 1991]. As a consequence of the stimulated lipolytic activity, the blood plasma levels of non-esterfied fatty acids can increase with more than 100%.

However, several side effects are associated with the use of lipolysis stimulating components for the reduction of body weight. Many of these problems have been disregarded until now.

One of the side effects of the use of components capable of stimulating lipolysis is a reduced insulin sensitivity. Reduced insulin sensitivity often leads to the disease diabetes, especially diabetes type II. As a consequence of reduced sensitivity, the human body starts to increase the secretion of insulin into the bloodstream, leading to enhanced levels of insulin in the blood plasma. Higher serum insulin levels are significantly associated with the development of metabolic manifestations like obesity.

SUMMARY OF THE INVENTION

The inventors have found that the above drawbacks can be solved by the coadministration of dill or an isolate thereof with a component capable of stimulating lipolysis. Hence, the present invention provides a method for the prevention and/or treatment of overweight in mammals which does not suffer from the above mentioned draw backs, i.e. the increase in insulin levels resulting from the ingestion of components capable of stimulating lipolysis, which method comprises the enteral administration to a mammal of a combination of dill or an isolate thereof and a component capable of stimulating in vivo lipolysis, wherein said component capable of stimulating in vivo lipolysis is preferably selected from the group consisting of methylxanthines, adrenergic amines, an isolate of *Paullinia cupana,* an isolate of *Zingziber officinale,* an isolate of *Camellia sinensis,* an isolate of *Ilex paraguayiensis* and mixtures thereof.

French patent application 2 793 657 describes a micronutritional product containing extremely small quantities of nutrients, said nutrients belonging to at least two of the categories of <<oligo-element>>, <<plant>>, <<food principle>> and <<vitamin>>. The application broadly teaches to utilise the individual nutrients in an amount between of $10^{-2}$ and $10^{-9}$ per litre solution. Example 17 describes a compressed product for apetite regulation that contains iron, zinc, magnesium, lime blossom, coriander, tarragon, garlic, extract of <<germe de blé germé>>, apricot, papaya, grapefruit, dill, pineapple, celery, rosemary, chicory, beer yeast, caraway, green tea, currant, vitamin B3, vitamin B6 and vitamin H.

The present invention also provides unit dosages, which can suitably be used in the treatment and/or prevention of overweight said dosage units containing dill or an isolate thereof and a component capable of stimulating lipolysis.

It is the inventor's belief that as a consequence of the ingestion of components capable of stimulating lipolysis, insulin levels will usually increase and as a result thereof an inhibitory feedback on the in vivo lipolysis will occur. Such effect is caused by the inhibitory effect of insulin on the breakdown of fat in adipose tissue through the inhibition of intracellular lipase. Consequently, lipolysis will be reduced and weight reduction and body fat reduction will be inhibited.

The side effects of the stimulation of in vivo lipolysis as a result of the administration of components capable of inducing in vivo lipolysis can be summarized as follows: (a) a risk of development of diabetes type II and (b) the reduction of the lipolysis stimulatory effect of lipolytic agents due to the feedback inhibition of intracellular lipase. It is an aspect of the present invention to provide a method for the treatment and/or prevention of overweight without these side effects.

It was surprisingly found by the inventors that dill or an isolate thereof is capable of reducing the above mentioned side effects of components capable of stimulating lipolysis. Without wishing to be bound by any theory, it is the inventors' belief that this is the result of the blood lipid lowering properties of dill. The lipid lowering effect of dill have been described by Yazdanparast, 2001 and Pakdaman (WO 01/24805 and DE-A 1 9633 446).

Following the administration of lipolytic agents, the blood lipid content increases due to the lipolysis of triacylglycerols stored in adipocytes and the subsequent release of free fatty acids (FFA) in the blood. High levels of triglycerides and free fatty acids in the blood have been associated with the induction of insulin resistance [Kruszynska, 2002; Mingrone, 1999; Polak, 2001]. As a consequence of reduced insulin sensitivity, the human body starts to increase the secretion of insulin into the bloodstream, leading to enhanced levels of insulin in the plasma [Ascaso, 2001].

The increase of free fatty acid concentration (FFA) in the blood caused by the action of the administered lipolytic agent thus contributes to the total pool of insulin-sensitivity reducing components (e.g. triacylglycerides, FFA etc.), which may subsequently result in diabetes type II. Decreased insulin sensitivity is accompanied by increased insulin levels, causing reduced in vivo lipolysis.

Blood lipids may be lowered by reducing adipocyte lipolysis. The present inventors discovered that dill and isolates thereof do not inhibit lipolysis, indicating that the blood lipid lowering effect of dill is not caused by an inhibition of lipolysis, making dill and isolate thereof suitable for counterbalancing the increase of blood lipids resulting from the administration of components capable of stimulating in vivo lipolysis.

DETAILED DESCRIPTION OF THE INVENTION

One aspect of the present invention relates to a method for the curative or prophylactic treatment of overweight in mammals, said method comprising the enteral administration to a mammal of a preparation comprising a combination of dill or isolate thereof and a component capable of stimulating in vivo lipolysis.

Another aspect of the present invention relates to a unit dosage comprising dill or an isolate thereof in an amount equivalent to between 5 and 10000 mg dill and a component capable of stimulating in vivo lipolysis, which unit dosage can suitably be used in a method for the treatment or prevention of overweight.

For the purpose of the present invention, the term unit dosage refers to a solid or semisolid solid entity, which is preferably selected from the group consisting of tablets, pills, microparticles, microspheres, suppositories, capsules, caplets and the like, which is suitable for unitary enteral administration to human subjects and other mammals, and wherein each unit contains a predetermined quantity of the present active principles and a pharmaceutically acceptable carrier. The term "isolate" as referred to in here, encompasses any fraction that can be obtained from a plant material by means of isolation techniques known in the art, e.g. extraction, distillation, squeezing etc. and that displays the desired functional properties described herein before. The term "extract" as used in the present invention refers to an isolate that has been obtained by means of solvent extraction.

Whenever reference is made to the term "component capable of stimulating in vivo lipolysis", this refers to any component or mixture of components that is capable of stimulating lipolysis in mammals.

The term "overweight" as used in the present invention refers to a body weight that is above the desired body weight of a human subject or that of a pet or farm animal as defined by its owner.

Dill

The plant name dill comes from the Saxon word "Dilla" which means soothe or the name 'dill' may come from the Norwegian word dill (to lull), referring to the plant's alleged carminative properties. The plant has long been taken as an aid to digestion and as a tranquillizer. Other ethnobotanical uses include the treatment of cough and the treatment of stomach upset.

Dill (*Anethum graveolens* or *Anethum sowa*) is a quick-growing herb, belonging to the Umbelliferae, with fine, ferny leaves on hollow, upright stems up to 3 feet high. The umbrella-like heads of yellow flowers are used for seasoning or fresh-cut flowers. Preferably *Anethum graveolens* is used in the present method.

Both dill and isolates of dill may be used in the method and preparation according to the present invention. The dill or isolate thereof as used in the present method can be obtained from whole plants or from one or more parts thereof, for example stems, stalks, leaf, roots, shoots, rhizomes, tubers, fruits, foliage, kernels, husks, hulls, seeds or mixtures thereof. According to a preferred embodiment the leaf of dill is used. Prior to use in the present method, the dill may be treated to improve handling characteristics, e.g. by comminuting, drying or sterilizing.

Dill Isolate

According to a particularly preferred embodiment, a dill isolate is used. The dill isolate can be obtained from whole plants or from one or more parts thereof, for example stems, stalks, leaf, roots, shoots, rhizomes, tubers, fruits, foliage, kernels, husks, hulls, seeds or mixtures thereof. According to a preferred embodiment the dill isolate is obtained from the dill leaf.

The dill isolate is preferably prepared by subjecting the dill plant or part thereof to one or more isolation processes selected from the group of solvent extractions, cold pressing, hot pressing, distillation, chromatography and filtering.

Dill Extract

Preferably the dill isolate used in the present invention is a dill extract. The dill extract is preferably prepared by the following procedure:
  A. Reducing dill raw material to yield a composition of particulate matter
  B. Contacting the particulate matter obtained in A with a suitable extraction solvent
  C. Incubation: keeping the particulate matter in contact with the solvent for a sufficiently long time to allow the transfer of soluble components from the particulate matter into the solvent.

D. Separating the insoluble particulate matter from the extract (extraction solvent containing the extracted soluble components)

E. Optionally, removing at least part of the solvent from the extract containing the extracted soluble components.

Reduction of the dill can be achieved by a variety of comminuting methods well known in the art, including cutting, crushing or grinding in a mill. Preferably, soon after the dill has been converted to particulate matter having a sufficiently small average diameter, e.g. below 1.5 mm in diameter, the dill particular matter is contacted with a suitable solvent. Preferred solvents include water, acetone, ethanol, chloroform, hexane, mixtures thereof and mixtures of any one of the previous mentioned solvents with water. Particularly preferred are mixtures of ethanol and water. Alternatively and equally preferred are solvents used in supercritical extraction processes such as carbondioxide and nitrogen.

In the preparation of the dill extract, the weight ratio solvent to dry dill particulate matter is preferably between 0.1 and 100, more preferably between 1 and 50, even more preferably between 2 and 25. In case the extract is obtained from a multiple step extraction process, this weight ratio is to be calculated on the basis of the total amounts of solvent and dry dill matter used in the preparation of the extract. The dill particulate matter is preferably suspended in the solvent for a sufficient time to extract soluble components therefrom (e.g. 0.5–20 hours). The suspension of the solvent and particulate matter may for example be subjected to agitation.

After incubation, the non-dissolved particulate matter is removed from the suspension, for example by centrifugation or filtration. The extract may, for example, be filtered with one or more filters having a pore size between 0.2–10 microns. Subsequently the liquid phase may be concentrated by removal of a part or all of the solvent. According to a preferred embodiment, at least 85% of the solvent is removed from the preparation. The solvent may for example be removed through distillation and/or by applying heat or vacuum.

The dill extract preferably has a concentration factor (the term "concentration factor" refers to the dry weight of the dill particulate material that was extracted divided by the dry weight of the dill extract obtained therefrom), is preferably between 2 and 100, more preferably between 5 and 50, even more preferably between 9 and 25.

Dosages of Dill or Isolates Thereof

The dill or isolate thereof is preferably administered in a daily amount that is equivalent to between 0.1 mg and 1000 mg dill per kg of body weight. According to a particularly preferred embodiment the dill or isolate thereof is administered in a daily amount that is equivalent to between 0.5 and 100 mg, more preferably between 1 and 25 mg dill per kg of body weight. For example, 5 mg dill extract with a concentration factor of 20 and a dry matter content of 95% is equivalent to 95 mg dill (as dry material).

The unit dosage according to the preset invention comprises dill or an isolate thereof in an amount equivalent to between 5 mg and 20 g dill. More preferably, the unit dosage comprises dill or isolate thereof in an amount between 5 and 10000 mg dill. More preferably, the unit dosage comprises dill or an isolate thereof in an amount equivalent to between 10 and 5000 mg, even more preferably between and 50 and 2000 mg, most preferably between 75 and 1000 mg dill.

Components Capable of Stimulating Lipolysis

The preparation used in the present method contains one or more components capable of stimulating in vivo lipolysis. Preferably this component is selected from the group consisting of methylxanthines, adrenergic amines, an isolate of *Paullinia cupana,* an isolate of *Zingziber officinale,* an isolate of *Camellia sinensis,* an isolate of *Ilex paraguayiensis,* isoprenaline and mixtures thereof. Preferably the component capable of stimulating in vivo lipolysis is plant derived. More preferably the component capable of stimulating in vivo lipolysis is obtained from plant material prepared with solvent extraction techniques.

The preferred methylxanthine used in the present method is caffeine. The term "adrenergic amines" refers to amines that are capable of directly replacing the adrenaline and noradrenaline in their actions on receptors and substances that stimulate the release of the endogenous adrenaline and noradrenaline. The preferred adrenergic amines used in the present method are synephrine, hordenine, octopamine, tyramine and N-methyltyramine.

Ginger

*Zingziber officinale* (ginger) is used as a spice in many diets and meals. Ginger belongs to the family Zingiberaceae. The ginger family is a tropical group especially abundant in Indo-Malaysia, consisting of more 1200 plant species in 53 genera. The genus *Zingiber* includes about 85 species of aromatic herbs from e.g. East Asia and tropical Australia.

The ginger plant is an erect perennial growing from one to three feet in height. The stem is surrounded by the sheathing bases of the two-ranked leaves. A club-like spike of yellowish, purple-lipped flowers have showy greenish yellow bracts beneath.

Ginger is known to moderately promote the secretion of catecholamines from cells, thereby moderately increasing plasma levels of the lipolysis-inducing catecholamines (Kawada, 1988), which is deemed to result in an increase in blood lipid levels and plasma insulin levels. It was found that dill or an isolate thereof can be used very effectively to counteract the side effects of ginger or isolates thereof.

According to a preferred embodiment the component capable of stimulating in vivo lipolysis used in the present invention is ginger extract. In the present invention, the ginger extract is preferably prepared from the rhizome of the plant. Preferably the ginger extract contains between about 1 and 50% gingerols and/or shogaols based on the dry weight of the extract, more preferably between 2 and 25%, even more preferably between 4 and 15%. The gingerols and/or shogoals promote the secretion of catecholamines from cells.

The ginger or isolate thereof is preferably administered in a daily amount that is equivalent to between 0.1 mg and 100 mg ginger per kg of body weight. According to a particularly preferred embodiment the ginger or isolate thereof is administered in a daily amount equivalent to between 0.5 and 100 mg, more preferably between 1 and 25 mg ginger per kg of body weight.

The unit dosage according to the present invention comprises ginger or an isolate thereof in an amount equivalent to between 5 mg and 20 g ginger. More preferably, the unit dosage comprises ginger or an isolate thereof in an amount that is equivalent to between 10 mg and 10 g, even more preferably between and 50 mg and 5 g, most preferably between 75 mg and 2 g ginger.

Caffeine

According to a further preferred embodiment the component capable of stimulating in vivo lipolysis is caffeine.

Caffeine is a well-known inhibitor of phosphodiesterase activity. Inhibition of this enzyme reduces the breakdown of noradrenaline-induced cAMP in the adipocyte, thereby prolonging the occurrence of high levels of cAMP in the adipocyte [Fredholm, 1984]. cAMP is involved in activating a phosphate kinase, which activates the hormone sensitive lipase (HSL). Prolonging the lifetime or increasing the concentration of cAMP in adipose tissue stimulates lipolysis by increasing the activity of the hormone sensitive lipase.

Ingestion of caffeine has been described to increase fatty acid concentration in plasma and to increase the rate of appearance of fatty acids, indicating enhanced lipolysis of triglycerides in adipose tissue [Arciero, 1995]. Additionally, caffeine ingestion results in a greater increase in insulin concentration during an oral glucose tolerance test [Graham, 2001], possibly by increased breakdown of glycogen [Miura, 1998].

Therefore oral administration of caffeine will contribute to the formation of insulin resistance by two mechanisms; a) increase blood FFA and b) increasing blood glucose level (glycemic status).

The caffeine used in the present invention may be naturally, semi-synthetically or synthetically derived. According to a preferred embodiment naturally derived caffeine is used. Preferred sources of naturally derived caffeine include herbal extracts comprising between 5 and 95% caffeine based on the dry weight of the herbal extract, more preferably between 10 and 50%. A preferred source of natural caffeine is *Paullinia cupana* extract.

Dill or isolates thereof can be used especially advantageously to counteract the side effects of caffeine in the present method.

The caffeine is preferably administered in a daily amount of between 0.1 mg and 25 mg per kg of body weight. According to a particularly preferred embodiment the caffeine is administered in a daily amount between 0.5 and 15 mg, more preferably between 1 and 10 mg caffeine per kg body weight.

The unit dosage according to the present invention preferably comprises between 5 and 4000 mg caffeine. More preferably between 10 and 4000 mg. More preferably, a unit dosage comprises between 25 and 2000 mg, even more preferably between and 50 and 1000 mg, most preferably between 100 and 500 mg caffeine.

*Camellia sinensis*

According to a further preferred embodiment the component capable of stimulating in vivo lipolysis is *Camellia sinensis* plant material or an isolate thereof.

*Camellia sinensis* has been shown to increase respiratory rate in rats, which is deemed to be caused by the lipolytic effects of extracts obtained from *Camellia sinensis*. Dill or isolates thereof can be used to reduce the adverse side effects of the lipolysis stimulating effects of *Camellia sinensis* plant material and isolates thereof.

The *Camellia sinensis* plant material or isolates thereof as used in the present invention may be fermented (black tea extract), semi-fermented (oolong tea extract) or non-fermented (green tea extract). According to a preferred embodiment black tea is used in the present invention. According to a further preferred embodiment an extract of *Camellia sinensis* is used.

The *Camellia sinensis* plant material or isolates thereof is preferably administered in a daily amount that is equivalent to between 0.1 mg and 100 mg *Camellia sinensis* per kg of body weight. According to a particularly preferred embodiment the *Camellia sinensis* plant material or isolates thereof is administered in a daily amount equivalent to between 0.5 and 100 mg, more preferably between 1 and 25 mg *Camellia sinensis* per kg of body weight.

The unit dosage according to the present invention comprises *Camellia sinensis* plant material or isolates thereof in an amount equivalent to between 5 mg and 20 g *Camellia sinensis*. More preferably, the unit dosage comprises *Camellia sinensis* plant material or isolates thereof in an amount equivalent to between 10 mg and 10 g, even more preferably between and 50 mg and 5 g, most preferably between 100 mg and 2 g *Camellia sinensis*.

Combinations

According to a further preferred embodiment, the component capable of stimulating in vivo lipolysis comprises at least two components selected from the group consisting of methylxanthines, adrenergic amines, an isolate of *Paullinia cupana,* an isolate of *Zingziber officinale,* an isolate of *Camellia sinensis,* an isolate of *Ilex paraguayiensis* and mixtures thereof.

A particularly advantageous combination for use in the present method is a combination of plant derived extracts comprising dill extract, an extract of *Zingziber officinale* and at least one extract selected from an extract of *Paullinia cupana* and an extract of *Camellia sinensis*.

Treatment and Prevention of Overweight

The present invention provides a method for reducing or preventing overweight, more preferably a method for the reduction of body fat. The present method is particularly suitable for humans. Human subjects who have a body mass index above 25 most advantageously use the present method. The present composition may also be advantageously used by overweight subjects suffering from diabetes, particularly suffering from diabetes type 2.

The present method is suitably used to reduce overweight or obesity, preferably to reduce body fat, and more preferably to stimulate lipolysis, to stimulate thermogenisis or to stimulate energy expenditure.

The term "energy expenditure" as used in the present invention refers to the metabolic rate of a mammal.

Packaged nutritional supplements and dietary products, which have been provided with labels that explicitly or implicitly direct the consumer towards the use of said supplement or product in accordance with one or more of the above or below purposes, are encompassed by the present invention. Such labels may for example make reference to the use in a method for the treatment of overweight by using terminology like "slim", "lean", "weight reduction", "fat-burning", "thermogenic" and the like. The overweight reducing properties of the product may be indicated via indicia such as pictures, drawings and other indicia from which a consumer can conclude that the product aims to treat or prevent overweight.

Administration

The preparation used in the present method can be applied in any suitable form, such as bars, pills, capsules, gels etc. According to a preferred embodiment the preparation is provided in a unit dosage form. The aforementioned unit dosage form is preferably in a solid or semisolid form, more preferably in the form of an oral dosage unit, which term includes pills, capsules, tablets, caplet, microparticles and microspheres. The solid or semisolid unit dosage form preferably has a weight between 0.1 and 30 grams, more preferably between 0.2 and 10 grams. The unit dosage may consist of one or more capsules, pill, tablets and the like, which contain either a single active ingredient or a combination of active ingredients. A unit dosage, if it consists of more than one physically distinct unit, is preferably administered to the subject within about 10 minutes, more preferably such unit dosage is ingested simultaneously. Preferably the unit dosage is comprised within one physically distinguishable unit. Preferably the distinct physical unit or units comprises a mixture of the present combination of active principles. The unit dosage preferably has a caloric value below 100 kcal, more preferably below 50 kcal. When an oral dosage unit is used to provide the active ingredients, it preferably has a weight between 0.2 and 4 grams, even more preferably between 0.5 and 3 grams. In the present method a daily dosage of the preparation as used in the present invention can include one or more pills, tablets, capsules and the like. Preferably the daily dosage consists of 1 to 6 pills, tablets or capsules.

Literature

Astrup A, Breum L, Toubro S, Hein P, Quaade F. The effect and safety of an ephedrine/caffeine compound compared to ephedrine, caffeine and placebo in obese subjects on an energy restricted diet. A double blind trial. Int J Obes Relat Metab Disord 1992; 16:269–77.

Galitzky J, Vermorel M, Lafontan M, Montastruc P, Berlan M. Thermogenic and lipolytic effect of yohimbine in the dog. Br J Pharmacol 1991; 104:514–8.

Yazdanparast R, Alavi M. Antihyperlipidaemic and antihypercholesterolaemic effects of *Anethum graveolens* leaves after the removal of furocoumarins. Cytobios 2001; 105: 185–91.

Kruszynska Y T, Worrall D S, Ofrecio J, Frias J P, Macaraeg G, Olefsky J M. Fatty acid-induced insulin resistance: decreased muscle PI3K, activation but unchanged Akt phosphorylation. J Clin Endocrinol Metab 2002; 87:226–34.

Mingrone G, Henriksen F L, Greco A V, et al. Triglyceride-induced diabetes associated with familial lipoprotein lipase deficiency. Diabetes 1999; 48:1258–63.

Polak K, Schmetterer L, Luksch A, et al. Free fatty acids/triglycerides increase ocular and subcutaneous blood flow. Am J Physiol Regul Integr Comp Physiol 2001; 280:R56–61.

Ascaso J F, Romero P, Real J T, Priego A, Valdecabres C, Carmena R. [Insulin resistance quantification by fasting insulin plasma values and HOMA index in a non-diabetic population]. Med Clin (Barc) 2001; 117:530–3.

Kawada T, Sakabe S, Watanabe T, Yamamoto M, Iwai K. Some pungent principles of spices cause the adrenal medulla to secrete catecholamine in anesthetized rats. Proc Soc Exp Biol Med 1988; 188:229–33.

Fredholm B B, Lindgren E. The effect of alkylxanthines and other phosphodiesterase inhibitors on adenosine-receptor mediated decrease in lipolysis and cyclic AMP accumulation in rat fat cells. Acta Pharmacol Toxicol (Copenh) 1984; 54:64–71.

Arciero P J, Gardner A W, Calles-Escandon J, Benowitz N L, Poehlman E T. Effects of caffeine ingestion on NE kinetics, fat oxidation, and energy expenditure in younger and older men. Am J Physiol 1995; 268:E1192–8.

Graham T E, Sathasivam P, Rowland M, Marko N, Greer F, Battram D. Caffeine ingestion elevates plasma insulin response in humans during an oral glucose tolerance test. Can J Physiol Pharmacol 2001; 79:559–65.

Miura T, Tatara M, Nakamura K, Suzuki I. Effect of guarana on exercise in normal and epinephrine-induced glycogenolytic mice. Biol Pharm Bull 1998; 21:646–8.

EXAMPLES

Example 1

Effect of Dill Extract on Lipolysis

A. Preparation of the Cells:

3T3-L1 cells were grown in T75 flasks. The cells were detached by trypsin incubation (±5 min at 37° C.). After detachment, 4 ml lipolysis standard medium was added to the flask (DMEM; 10% fetal calf serum; 4.5 g/l D-glucose; 100 U/ml penicillin; 100 µg/ml streptomycin) and the cells were suspended therein. The cell suspension was then diluted in lipolysis standard medium to 50000 cells/ml (5000 cells/100 µl), and 100 µl of this diluted cell mix was transferred to a precoated well in a 96 wells plate. (Preparation of precoated 96 well plate: 50 µl 1% gelatin in demineralized water was added to each well of the 96 well plate and incubated for 10 minutes at 37° C. Thereafter the solution was removed).

After incubation for 48 hours at 37° C., the medium was refreshed (removal of old medium and addition of 100 µl lipolysis standard medium) and the cells incubated at 37° C. After 72 hours, the supernatant was removed and 100 µl differentiation medium (5 µg/ml bovine insuline; 0.25 µM dexamethasone; 0.5 mM IBMX; in standard medium) was added. After 48 hours incubation at 37° C. in the differentiation medium, the supernatant was removed and 100 µl insulin medium (5 µl/ml bovine insulin in standard medium) was added to each well. After 48 hours incubation at 37° C. in insulin medium, the supernatant was removed and 100 µl standard medium is added to each well. After 72 hours incubation at 37° C. in standard medium, the supernatant was removed and the test samples were added.

B. Preparation of the Samples

Sample A: 10 µl of a solution of dill extract (obtained by diluting 200 µg dill extract 1:20 ex Triarco Industries, Wayne, USA in 1 ml DMEM) was mixed with 90 µl lipolysis standard medium containing isoprenaline. The isoprenaline end concentration in the sample was $1 \times 10^{-7}$ M.

Sample B: 10 µl isoprenaline ($1 \times 10^{-6}$ M) was mixed with 90 µl lipolysis standard medium. The isoprenaline end concentration in the sample was $1 \times 10^{-7}$ M.

C. Testing for Lipolysis Stimulating Activity

The medium in the 96-well plate with differentiated 3T3-cells was aspirated, followed by the addition of 90 µl of standard lipolysis medium and 10 µl sample. After 24 hours incubation at 37° C., the glycerol concentration in the supernatant was determined using a glycerol assay (Sigma Cat.no. 337) against a standard curve of glycerol in lipolysis standard medium.

D. Calculation of Relative Lipolysis Stimulating Activity

The relative lipolysis inhibiting activity of the dill extract was calculated by dividing the glycerol formation of sample A of interest by the glycerol formation of sample B.

E. Results

It was found that dill extract does not reduce lipolysis in cells wherein the lipolysis is stimulated by a lipolysis stimulating agent (see Table 1)

TABLE 1

| | Relative lipolysis inhibiting effect |
|---|---|
| 1 × 10$^{-8}$ isoprenaline | 1 |
| dill extract and × 10$^{-8}$ isoprenaline | 1.01 |

Example 2

Composition for Use in Weight Management Program

A single unit dosage in the form of two capsules providing on a daily base;
  5 mg dill extract with a concentration factor of 20 [Triarco Industries, Wayne, USA]
  100 mg extract of *Zingziber officinale* containing 5 wt. % gingerols [Finzelberg, Andernach, Germany]
  550 mg *Paullinia cupana* extract, 36 wt. % caffeine [Triarco Industries, Wayne, USA]

Example 3

Effects of Dill Extract and Caffeine on Energy Expenditure in Rats.

6 months old male Wistar rats were placed in metabolic cages (Oxymax Equal Flow System, Columbus Instruments, Ohio, USA) at 8.30 a.m. (lights on at 7.00 a.m.). Oxygen and carbon dioxide concentrations were monitored and energy expenditure (EE=Calorific value*VO$_2$=(3.815+1.232×RQ) *VO2) was calculated therefrom.

First, basal metabolism was measured during 2½ hours. Next, at 11.00 a.m. the animals were shortly removed from the metabolic cage; water (treatment A); 12.5 mg/kg caffeine (Sigma-Aldrich Chemie)+50 mg/kg dill extract (*Anethum graveolens*, Triarco Industries, Inc) (treatment B); or 12.5 mg/kg caffeine (Sigma-Aldrich Chemie)+200 mg/kg dill extract (*Anethum graveolens*, Triarco Industries, Inc) (treatment C) was administered in a volume of 1 ml water via oral gavage; and the animals were placed back in the metabolic cage. Subsequently, the effects of the treatment on oxygen consumption and CO$_2$-production were monitored during 4 hours. The O$_2$- and CO$_2$-concentrations in each cage were measured every 26 minutes.

The set-up of the experiment was a crossover design. Water as well as the combinations of 12.5 mg caffeine with either 50 or 200 mg dill extract per kg body weight were each tested in n=6 rats. The animals were used as their own control by administering vehicle (water) the week before or after administration of the test components.

FIG. 1 depicts the effects of treatments A, B and C on energy expenditure. The basal energy expenditure was set at zero; the change in energy expenditure after treatment compared to basal energy expenditure is shown in FIG. 1. Data were analysed statistically with General Linear Model—repeated measures. The results show a significant increase in energy expenditure by treatment compared to treatment A; a significantly increase in energy expenditure by treatment C compared to treatment A; and a significantly increased energy expenditure by treatment C compared to Treatment B. FIG. 1 also shows the prolonged elevation of an increased energy expenditure after treatment C compared to treatment B.

These results are indicative for the energy expenditure stimulating effects, thermogenesis increasing effects and weight reducing properties of dill extract and a component stimulating in vivo lipolysis, e.g. caffeine.

Furthermore, the results show the surprising the prolonged elevation of an increased energy expenditure following the administration of a component capable of stimulating in vivo lipolysis (e.g. caffeine) and dill (e.g. dill extract), which are indicative for an improved weight reducing effect and thermogenic effect. Maintaining an elevated energy expenditure for a prolonged period will result in the increased burning of calories, and faster weight reduction. In a further aspect the present example shows that through coadministration of dill (e.g. dill extract) with a component capable of stimulating in vivo lipolysis, the same body weight reduction can be achieved with a reduced amount components capable of stimulating in vivo lipolysis (e.g. caffeine) and/or more body weight reduction can be achieved with the same amount of components capable of stimulating in vivo lipolysis.

For the determination of the extent to which the treatments A, B and C increases energy expenditure, basal energy expenditure (determined by area under the curve calculation of the basal measurements) was subtracted from the energy expenditure after component administration (also area under the curve calculation), yielding a measure of the increase in energy expenditure caused by the different treatments.

The energy expenditure response to test component administration was analysed with a paired-samples t-test.

Table 2 shows a significant increase in energy expenditure in rats that received Treatment B or C compared to treatment A and a significant increase of energy expenditure in rats that received Treatment C compared to Treatment B. The results are indicative for the energy expenditure stimulating effects, thermogenesis increasing effects and weight reducing properties of the combination of dill extract and a component stimulating in vivo lipolysis, e.g. caffeine. The results are further indicative for the synergistic energy expenditure stimulating effects of dill and caffeine.

TABLE 2

The increase in energy expenditure (EE) by caffeine + dill administration.

| Treatment | Test component | Increase in EE (kcal/h) during 260 minutes |
|---|---|---|
| Treatment A | Water (control) | 0.051 ± 0.062 |
| Treatment B | Caffeine (12.5 mg/kg) + Dill (50 mg/kg) | 0.343 ± 0.068* |
| Treatment C | Caffeine (12.5 mg/kg) + Dill (200 mg/kg) | 0.516 ± 0.050*# |

*P<0.05, compared to water control.
P<0.05, compared to caffeine + dill (50 mg/kg).

Example 4

Effects of Dill Extract and Caffeine on Body Weight of Rats.

Animals 16 male Wistar rats (age 10 weeks at the start of the experiments) were housed individually. The animals had free access to water and food. During the study body weight and food intake were monitored.

Diets

The first week, all animals were fed a semi-synthetic high fat diet (HFD, 30% of energy from fat, based on the AIN-93M diet, Research Diets Services BV, Wijk bij Duurstede, The Netherlands, see Table 3).

TABLE 3

Diet composition (all components weight by weight)

| Component | Control High fat diet |
|---|---|
| Casein | 140.0 |
| Cornstarch | 378.4 |
| Dyetrose | 126.0 |
| Sucrose | 81.3 |
| Cellulose | 50.0 |
| Beef fat | 60.0 |
| Soybean Oil | 115.0 |
| t-Butylhydroquinone | 0.008 |
| L-Cystine | 1.8 |
| Choline Bitartrate | 2.5 |
| Vitamin Mix | 10.0 |
| Mineral Mix | 35.0 |

Body weight was monitored 3 times a week. After this run-in period, the animals were divided in two groups (n=8) with equal average body weight. At Time=0 days, one group received the high fat diet with 1.5 g caffeine (Sigma-Aldrich Chemie) per kg diet. The other group received the high fat diet containing 1.5 g caffeine per kg diet and 1.0 g dill extract (*Anethum graveolens*, Triarco Industries, Inc.) per kg diet. The caffeine and dill extract were mixed in the diet. These concentrations in the diet result in an average dosage of 75 mg caffeine/kg body weight per day and 50 mg dill extract/kg body weight per day. During 2½ weeks on these diets, body weight was monitored on weekdays.

Figure 2:
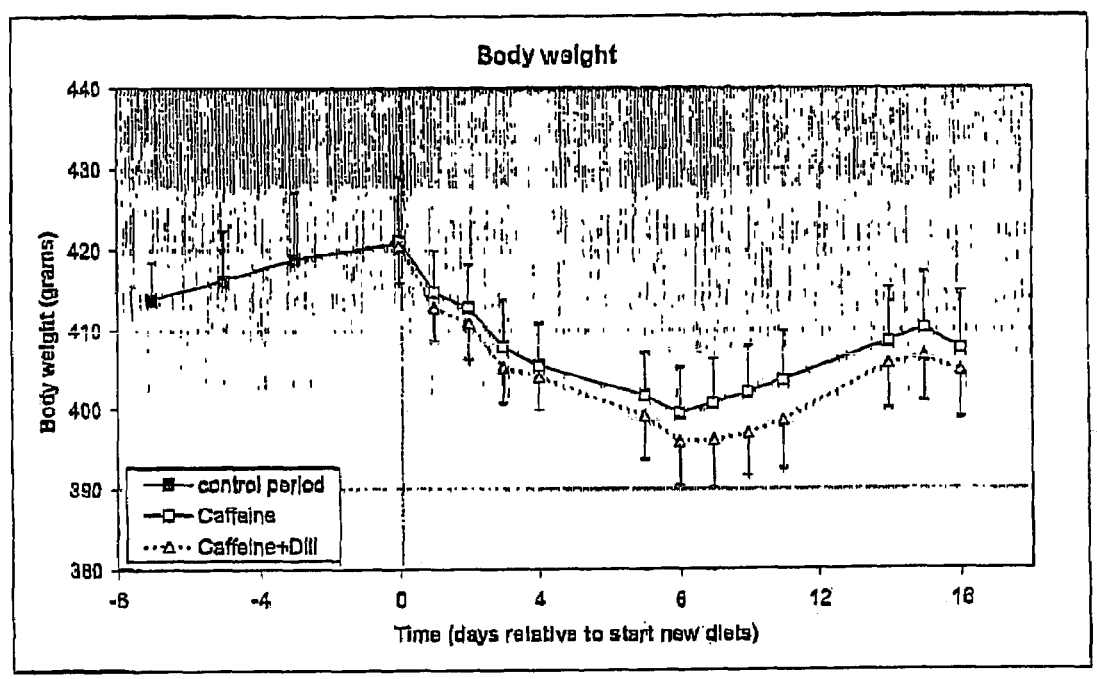

FIG. 2 depicts the body weight of rats that received either caffeine or the combination of caffeine and dill extract. FIG. 1 shows a trend for reduced body weight of the rats that received caffeine and dill extract compared to caffeine alone. The results are indicative for the synergistic weight reducing properties of dill extract when combined with caffeine.

Example 5

Effects of Dill Extract and Caffeine on Plasma Glucose and Plasma Insulin Levels A (long term) side effects of the use of components capable of stimulating lipolysis is a reduced insulin sensitivity. Reduced insulin sensitivity often leads to the disease diabetes, especially diabetes type 2. As a consequence of reduced sensitivity, the human body starts to increase the secretion of insulin into the bloodstream, leading to enhanced levels of insulin in the blood plasma. Higher serum insulin levels are significantly associated with the development of metabolic manifestations like obesity. The effects caffeine and caffeine+dill on blood glucose levels and blood insulin levels were investigated.

The rats were grown and treated as described in Example 4.

A blood sample was draw by tail incision after 1 week on the high fat diet and after 2½ weeks of treatment with caffeine or caffeine+dill extract (see Example 5). Blood was collected in heparinised and paraoxon-coated eppendorf cups. Plasma was kept at −20° C. until further analysis.

Plasma glucose was measured in the samples with an oxidase-peroxidase method in 96 wells format (Roche Diagnostics, #1448668). Plasma insulin was measured with a radioimmunoassay (RIA, Linco), according to the kit protocol.

Figure 3:
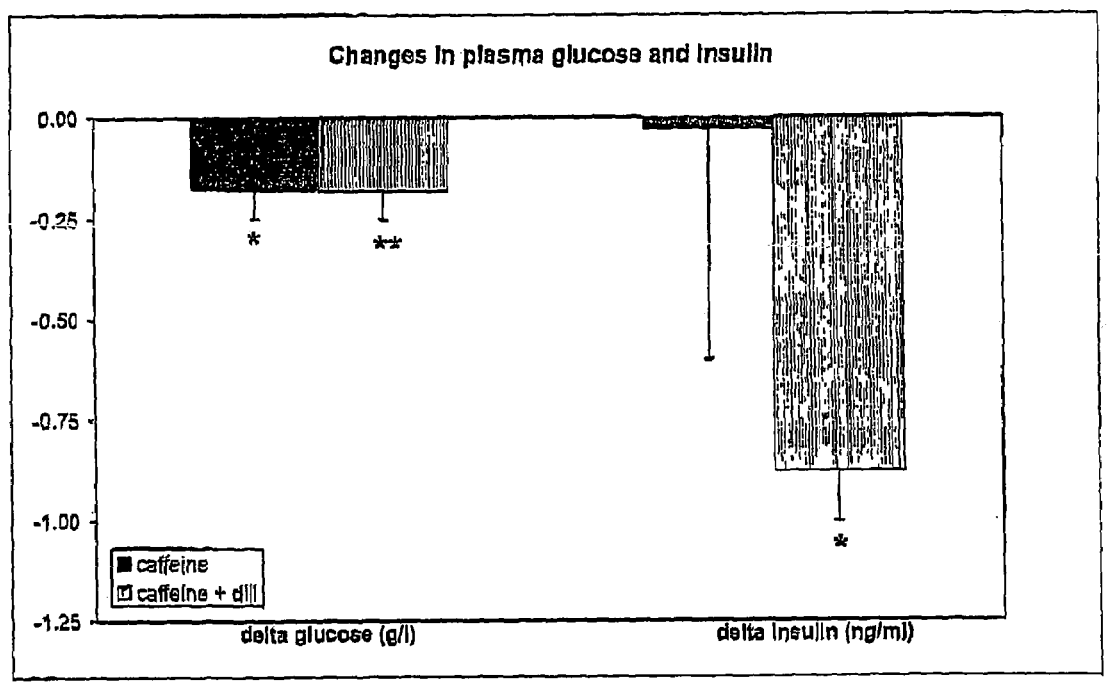

FIG. 3 Shows:
  I. A significant reduction of plasma glucose levels in the groups receiving caffeine and caffeine+dill. The reduction being similar for both groups.
  II. A significant reduction of plasma insulin levels in the groups receiving caffeine+dill extract. The group receiving caffeine shows no reduction in plasma insulin levels.

The significantly reduced plasma insulin levels in the group receiving caffeine+dill extract in combination with the absence of such a reduction in the group receiving caffeine only (while having similar reduction in blood glucose levels) are indicative for the beneficial effects of dill extract on the effects of caffeine, the insulin resistance preventive effects of dill extract and the diabetes type 2 preventive effects of dill extract.

Example 7

Thermogenic Composition for Use in Weight Management Program

A single unit dosage in the form of two capsules providing on a daily base:
  10 mg dill extract with a concentration factor of 20 [Triarco Industries, Wayne, USA]
  100 mg caffeine (Sigma Chemicals)
  100 mg extract of *Zingziber officinale* containing 5 wt. % gingerols [Finzelberg, Andernach, Germany]
  100 mg extract of *Camellia sinensis* (GCI Nutrients, Burlingame, Calif. USA)

Example 8

Thermogenic Composition for Use in Weight Management Program

A unit dosage in the form of a capsule providing on a daily base:
  500 mg Yerba Mate Dry extract (8%) (P L Thomas, Morristown, N.J., USA)
  3 mg dill extract with a concentration factor of 20 [Triarco Industries, Wayne, USA]
  150 mg caffeine (Sigma Chemicals)

The invention claimed is:

1. A solid or semisolid unit dosage selected from the group consisting of tablets, pills, microparticles, microspheres, suppositories, capsules and caplets, that is suitable for enteral unitary administration to human subjects and other mammals comprising:
  a. dill or an extract thereof in an amount equivalent to between 5 mg and 20 g dill;
  b. between 10 and 4000 mg caffeine; and
  c. between 5 mg and 20 g *Camellia sinensis*.

2. The unit dosage according to claim 1, wherein the *Camellia sinensis* is in a daily dosage unit of 0.1 mg –100 mg per kg of body weight.

3. A solid or semi-solid unit dosage for enteral unitary administration to human subjects and other mammals comprising:
  a. dill or an extract thereof in an amount equivalent to between 5 mg and 20 g dill;
  b. between 10 and 4000 mg caffeine;

c. between 5 mg and 20 g *Camellia sinensis*; and d. a pharmaceutically acceptable carrier.

4. The unit dosage according to claim 3 wherein the *Camellia sinensis* is in a daily dosage unit of 0.1 mg–100 mg per kg of body weight.

5. A solid or semi-solid unit dosage comprising:

a combination of between 5 mg and 20 g dill or an extract thereof, between 10 and 4000 mg caffeine, and between 5 mg and 20 g *Camellia sinensis* in a unit form selected from the group consisting of tablets, pills, microparticles, microspheres, suppositories, capsules and caplets.

6. The unit dosage according to claim 5 wherein the *Camellia sinensis* is in a daily dosage unit of 0.1 mg–100 mg per kg of body weight.

* * * * *